United States Patent
Ishii et al.

(10) Patent No.: US 6,548,713 B2
(45) Date of Patent: Apr. 15, 2003

(54) PROCESS FOR THE PREPARATION OF ORGANIC COMPOUNDS WITH MANGANESE CATALYSTS OR THE LIKE

(75) Inventors: Yasutaka Ishii, Takatsuki (JP); Takahiro Iwahama, Suita (JP); Satoshi Sakaguchi, Suita (JP); Tatsuya Nakano, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/959,843

(22) PCT Filed: Mar. 8, 2001

(86) PCT No.: PCT/JP01/01813

§ 371 (c)(1),
(2), (4) Date: Nov. 9, 2001

(87) PCT Pub. No.: WO01/66501

PCT Pub. Date: Sep. 13, 2001

(65) Prior Publication Data

US 2002/0165416 A1 Nov. 7, 2002

(30) Foreign Application Priority Data

Mar. 10, 2000 (JP) .......................................... 2000-67679

(51) Int. Cl.[7] .......................... C07C 45/32; C07C 45/45

(52) U.S. Cl. ....................................... 568/458; 568/465

(58) Field of Search .................................. 568/458, 465

(56) References Cited

U.S. PATENT DOCUMENTS 4,322,561 A    3/1982  Faggian et al.

FOREIGN PATENT DOCUMENTS

| GB | 1134951 | 11/1968 |
|---|---|---|
| JP | A7-247224 | 9/1995 |
| WO | A1 97/28897 | 8/1997 |

*Primary Examiner*—Taofiq Solola
(74) *Attorney, Agent, or Firm*—Birch, Stewart, Kolasch & Birch, LLP

(57) ABSTRACT

The process of this invention efficiently produces a compound having an alkyl group or alkenyl group bonded at the alpha position of an electron attractive group, or a derivative thereof, by catalytic radical addition reaction. The process reacts a compound containing an electron attractive group of Formula (1) as defined in the specification with a compound containing an unsaturated carbon-carbon bond of Formula (2) or (7) as defined in the specification to produce a compound of Formula (3) or (8) as defined in the specification. The invention is characterized by carrying out the reaction in the presence of oxygen and a catalytic compound of a Group 7, 8, or 9 element of the Periodic Table of Elements.

8 Claims, No Drawings

PROCESS FOR THE PREPARATION OF ORGANIC COMPOUNDS WITH MANGANESE CATALYSTS OR THE LIKE

This application is the national phase under 35 U.S.C. § 371 of PCT International Application No. PCT/JP01/01813 which has an International filing date of Mar. 8, 2001, which designated the United States of America.

TECHNICAL FIELD

The present invention relates to a process for producing organic compounds such as carbonyl compounds that are useful as, for example, perfumes, paint additives, additives for resin modification, pharmaceuticals, agrochemicals, and other fine chemicals or raw materials therefor.

BACKGROUND ART

Processes for producing addition compounds are widely known, in which a radical is generated at the alpha position of an electron attractive group of a compound containing the electron attractive group, such as a ketone, and then the formed radical adds to, for example, an olefin to yield a corresponding addition compound. Metallic oxidizing agents such as Mn(III) salts have conventionally been used in this reaction. However, in this type of processes, the used metallic oxidizing agent itself is reduced to proceed an addition reaction, and the process requires a large amount of the metallic oxidizing agent and requires much effort and high cost for treating heavy metal salts after the reaction. In addition, the process using stoichiometric amounts of the metallic oxidizing agent results in low reaction selectivity and cannot significantly produce a corresponding adduct in a high yield.

DISCLOSURE OF INVENTION

Accordingly, an object of the present invention is to provide a process for efficiently producing a compound having an alkyl group or alkenyl group bonded at the alpha position of an electron attractive group, or a derivative thereof, by catalytic radical addition reaction.

Another object of the present invention is to provide a process for producing a compound having an alkyl group or alkenyl group bonded at the alpha position of an electron attractive group, or a derivative thereof, with a high selectivity from a compound having the electron attractive group, such as a ketone, and a compound having an unsaturated carbon-carbon bond.

A further object of the present invention is to provide a process for producing a ketone having an alkyl group or alkenyl group bonded at the alpha position of a carbonyl group from a hydrocarbon having a methylene group through one pot.

After intensive investigations to achieve the above objects, the present inventors have found that, when a compound of a Group 5, 6, 7, 8 or 9 element of the Periodic Table of Elements and oxygen are used in combination, they act as an oxidizing agent and a catalyst, respectively, and thereby efficiently yield a corresponding adduct from a compound having an electron attractive group and a compound having an unsaturated carbon-carbon bond (an olefin or an acetylene). The present invention has been accomplished based on these findings.

Specifically, the present invention provides a process for producing an organic compound, the process including the step of allowing a compound containing an electron attractive group represented by following Formula (1):

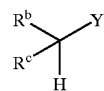

(1)

wherein Y is an electron attractive group; and $R^b$ and $R^c$ are each independently a hydrogen atom or an organic group, where Y, $R^b$ and $R^c$ may respectively be combined with each other to form a ring with an adjacent carbon atom, to react with a compound containing an unsaturated carbon-carbon bond represented by following Formula (2) or (7):

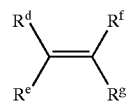

(2)

(7)

wherein $R^d$, $R^e$, $R^f$, $R^g$, $R^i$ and $R^j$ are each independently a hydrogen atom or an organic group, where $R^d$, $R^e$, $R^f$ and $R^g$ may respectively be combined with each other to form a ring with one or two adjacent carbon atoms, and $R^i$ and $R^j$ may be combined with each other to form a ring with adjacent two carbon atoms, in the presence of oxygen and a catalytic compound of a Group 5, 6, 7, 8 or 9 element of the Periodic Table of Elements to yield a compound represented by following Formula (3) or (8):

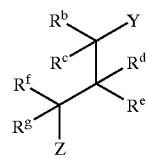

(3)

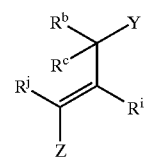

(8)

wherein Z is a hydrogen atom or a hydroxyl group; and Y, $R^b$, $R^c$, $R^d$, $R^e$, $R^f$, $R^g$, $R^i$ and $R^j$ have the same meanings as defined above.

The present invention also provides a process for producing an organic compound, the process including the step of allowing a carbonyl-group-containing compound represented by following Formula (1a):

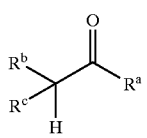

(1a)

wherein $R^a$ is a hydrogen atom or an organic group; and $R^b$ and $R^c$ are each independently a hydrogen atom or an organic group, where $R^a$, $R^b$ and $R^c$ may respectively be combined with each other to form a ring with adjacent one or two carbon atoms, to react with an olefin represented by following Formula (2a)

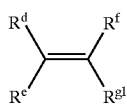
(2a)

wherein $R^d$, $R^e$ and $R^f$ are each independently a hydrogen atom or an organic group; and $R^{g1}$ is an aromatic cyclic group, where $R^d$, $R^e$, $R^f$ and $R^{g1}$ may respectively be combined with each other to form a ring with one or two adjacent carbon atoms, in the presence of oxygen and a catalytic compound of a Group 5, 6, 7, 8 or 9 element of the Periodic Table of Elements to yield a furanol derivative represented by following Formula (4):

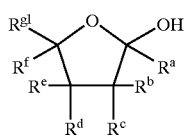
(4)

wherein $R^a$, $R^b$, $R^c$, $R^d$, $R^e$, $R^f$ and $R^{g1}$ have the same meanings as defined above.

In addition and advantageously, the present invention provides a process for producing an organic compound, the process including the step of allowing a compound containing a methylene group represented by following Formula (5):

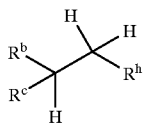
(5)

wherein $R^b$, $R^c$ and $R^h$ are each independently a hydrogen atom or an organic group, where $R^b$, $R^c$ and $R^h$ may respectively be combined with each other to form a ring with adjacent one or two carbon atoms, to react with a compound having an unsaturated carbon-carbon bond represented by following Formula (2) or (7):

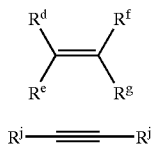
(2)

(7)

wherein $R^d$, $R^e$, $R^f$, $R^g$, $R^i$ and $R^j$ are each independently a hydrogen atom or an organic group, where $R^d$, $R^e$, $R^f$ and $R^g$ may respectively be combined with each other to form a ring with one or two adjacent carbon atoms, and $R^i$ and $R^j$ may be combined with each other to form a ring with adjacent two carbon atoms, in the presence of oxygen, a catalytic compound of a Group 5, 6, 7, 8 or 9 element of the Periodic Table of Elements and an imide compound represented by following Formula (6):

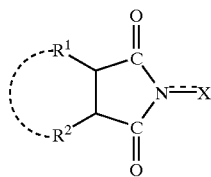
(6)

wherein $R^1$ and $R^2$ are the same or different and are each a hydrogen atom, a halogen atom, an alkyl group, an aryl group, a cycloalkyl group, a hydroxyl group, an alkoxy group, a carboxyl group, an alkoxycarbonyl group or an acyl group, where $R^1$ and $R^2$ may be combined to form a double bond -or an aromatic or non-aromatic ring; X is an oxygen atom or a hydroxyl group; and one or two of N-substituted cyclic imido group indicated in the formula may be further formed on $R^1$, $R^2$, or on the double bond or aromatic or non-aromatic ring formed together by $R^1$ and $R^2$, to yield a carbonyl compound represented by following Formula (3a) or (8a)

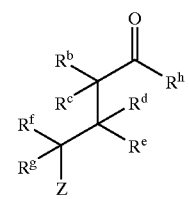
(3a)

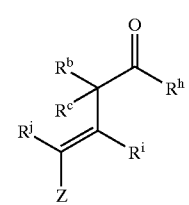
(8a)

wherein Z is a hydrogen atom or a hydroxyl group; and $R^b$, $R^c$, $R^h$, $R^d$, $R^e$, $R^f$, $R^g$, $R^i$ and $R^j$ have the same meanings as defined above.

The term "organic group" in the present description is used in a broad meaning including groups each containing a non-metallic atom in addition to carbon-atom-containing groups. Such groups each containing a non-metallic atom include, for example, halogen atoms, hydroxyl group, mercapto group, amino group, nitro group and sulfonic acid group.

BEST MODE FOR CARRYING OUT THE INVENTION

[Compounds Containing Electron Attractive Groups]

The compounds represented by Formula (1) for use as raw materials in the present invention include a wide variety of chain or cyclic compounds each having an electron attractive group in a molecule. Such compounds include, but are not limited to, ketones and derivatives thereof having a protected carbonyl group, aldehydes and derivatives thereof having a protected carbonyl group, esters, lactones, carboxylic acids, amides, lactams, nitrites, imino compounds and nitro compounds.

In Formula (1), electron attractive groups in Y are not specifically limited and include, for example, formyl, acetyl, propionyl, butyryl, (meth)acryloyl, cyclopentanecarbonyl, cyclohexanecarbonyl, benzoyl, naphthoyl, pyridinecarbonyl, and other aliphatic, alicyclic, aromatic or heterocyclic acyl groups and derivatives thereof having a protected carbonyl group; methoxycarbonyl, ethoxycarbonyl, isopropoxycarbonyl, butoxycarbonyl, vinyloxycarbonyl, cyclopentyloxycarbonyl, cyclohexyloxycarbonyl, phenoxycarbonyl, benzyloxycarbonyl, pyridyloxycarbonyl, acyloxycarbonyl group (acid anhydride group), and other substituted oxycarbonyl groups; carboxyl group; carbamoyl, N-methylcarbamoyl, N-phenylcarbamoyl, N,N-dimethylcarbamoyl, 1-pyrrolidinylcarbonyl, piperidinocarbonyl, and other substituted or unsubstituted carbamoyl groups; cyano group; substituted or unsubstituted iminoalkyl groups; nitro group; sulfonic acid group, sulfinic acid group, and other sulfur acid groups; methyl sulfonate, ethyl sulfonate, methyl sulfinate, ethyl sulfinate, and other sulfur acid ester groups (sulfonic ester groups and sulfinic ester groups); phenyl, naphthyl, and other aryl groups; 3-pyridyl and other aromatic heterocyclic groups; vinyl, 1-propenyl, ethynyl, and other 1-alkenyl or 1-alkynyl groups; and trifluoromethyl and other haloalkyl groups. Protected derivatives of the acyl groups include derivatives in which the carbonyl group is protected with a conventional protective group, such as dimethylacetal, diethylacetal, 1,3-dioxane, 1,3-dioxolane, and other acetals; and S,S'-dimethyldithioacetal and other dithioacetals.

Organic groups in $R^b$ and $R^c$ may be any groups, as far as they do not adversely affect the reaction, and include, for example, hydrocarbon groups, heterocyclic groups, hydroxyl group, mercapto group, alkoxy groups, halogen atoms, N-substituted or unsubstituted amino groups, and the aforementioned electron attractive groups. The hydroxyl group, carboxyl group and amino groups may be protected with a conventional protective group.

The hydrocarbon groups include aliphatic hydrocarbon groups, alicyclic hydrocarbon groups and aromatic hydrocarbon groups. Such aliphatic hydrocarbon groups include, but are not limited to, methyl, ethyl, propyl, isopropyl, butyl, isobutyl, s-butyl, t-butyl, pentyl, hexyl, octyl, decyl, tetradecyl, hexadecyl, octadecyl, allyl, and other straight- or branched-chain aliphatic hydrocarbon groups (alkyl groups, alkenyl groups and alkynyl groups) each having from about 1 to about 20 (preferably from about 1 to about 10, and more preferably from about 1 to about 6) carbon atoms.

The alicyclic hydrocarbon groups include, but are not limited to, cyclopropyl, cyclobutyl, cyclopentyl, cyclohexyl, cyclohexenyl, cyclooctyl, cyclodecyl, cyclododecyl, and other alicyclic hydrocarbon groups (e.g., cycloalkyl groups and cycloalkenyl groups) each having from about 3 to about 20 carbon atoms (preferably from about 3 to about 15 carbon atoms).

The aromatic hydrocarbon groups include, but are not limited to, phenyl, naphthyl, and other aromatic hydrocarbon groups each having from about 6 to about 20 carbon atoms.

These hydrocarbon groups may have various substituents. Such substituents include, for example, halogen atoms (e.g., fluorine, chlorine, bromine and iodine atoms), oxo group, hydroxyl group which may be protected with a protective group, hydroxymethyl group which may be protected with a protective group, amino group which may be protected with a protective group, carboxyl group which may be protected with a protective group, substituted oxycarbonyl groups, substituted or unsubstituted carbamoyl groups, nitro group, acyl groups, cyano group, alkyl groups (e.g., methyl, ethyl, and other $C_1$–$C_4$ alkyl groups), cycloalkyl groups, aryl groups (e.g., phenyl and naphthyl groups) and heterocyclic groups. Conventional protective groups in the field of organic synthesis can be used as the protective groups.

Heterocyclic rings constituting heterocyclic groups in $R^b$ and $R^c$ include aromatic heterocyclic rings and non-aromatic heterocyclic rings. Such heterocyclic rings include, but are not limited to, heterocyclic rings each containing an oxygen atom as a hetero atom (e.g., furan, tetrahydrofuran, oxazole, isoxazole, and other 5-membered rings; 4-oxo-4H-pyran, tetrahydropyran, morpholine, and other 6-membered rings; benzofuran, isobenzofuran, 4-oxo-4H-chromene, chroman, isochroman, and other condensed rings), heterocyclic rings each containing a sulfur atom as a hetero atom (e.g., thiophene, thiazole, isothiazole, thiadiazole, and other 5-membered rings; 4-oxo-4H-thiopyran and other 6-membered rings; benzothiophene and other condensed rings), heterocyclic rings each containing a nitrogen atom as a hetero atom (e.g., pyrrole, pyrrolidine, pyrazole, imidazole, triazole, and other 5-membered rings; pyridine, pyridazine, pyrimidine, pyrazine, piperidine, piperazine, and other 6-membered rings; indole, indoline, quinoline, acridine, naphthyridine, quinazoline, purine, and other condensed rings). These heterocyclic groups may have substituents such as the substituents which the hydrocarbon groups may have.

In $R^b$ and $R^c$, alkoxy groups include, but are not limited to, methoxy, ethoxy, propoxy, butoxy, and other alkoxy groups each having from about 1 to about 6 carbon atoms. Halogen atoms include fluorine, chlorine, bromine and iodine atoms. N-substituted amino groups include, for example, N,N-dimethylamino, N,N-diethylamino and piperidino groups.

Two of the substituents Y, $R^b$ and $R^c$ may be combined with each other to form a ring with an adjacent carbon atom. Rings formed by $R^b$ and $R^c$ with the adjacent carbon atom include, but are not limited to, cyclopropane, cyclobutane, cyclopentane, cyclopentene, cyclohexane, cyclohexene, cyclooctane, cyclodecane and cyclododecane rings, decalin ring, adamantane ring, and other non-aromatic carbon rings (cycloalkane rings, cycloalkene rings and bridged carbon rings) each having from about 3 to about 20 members (preferably from about 3 to about 15 members, more preferably from about 5 to about 15 members, and typically preferably from about 5 to about 10 members). These rings may have substituents such as the substituents which the hydrocarbon groups may have. Separately, other rings (non-aromatic rings or aromatic rings) may be condensed with these rings.

Rings formed by Y and $R^b$ or $R^c$ with the adjacent carbon atom include, but are not limited to, cyclopentanone ring, cyclohexanone ring, cyclooctanone ring, cyclodecanone ring, cyclododecanone ring, adamantanone ring, and other non-aromatic carbon rings (cycloalkanone rings, cycloalkenone rings and oxo-group-containing bridged carbon rings) each having an oxo group bonded thereto and having from about 3 to about 20 members (preferably from about 3 to about 15 members, more preferably from about 5 to about 15 members, and typically preferably from about 5 to about 10 members) [in this case, the compound (1) constitutes a cyclic ketone]; β-propiolactone ring, γ-butyrolactone ring, δ-valerolactone ring, ε-caprolactone ring, and other lactone rings each having from about 4 to about 20 members (preferably from about 4 to about 15 members, and more preferably from about 5 to about 7 members) [in this case, the compound (1) constitutes a lactone]; and lactam rings corresponding to the lactone rings [in this case, the compound (1) constitutes a lactam]. These rings may have substituents such as the substituents which the hydrocarbon groups may have. Separately, other rings (non-aromatic rings or aromatic rings) may be condensed with these rings.

Preferred substituents $R^b$ and $R^c$ include, for example, hydrogen atom, $C_1$–$C_{10}$ aliphatic hydrocarbon groups (e.g., methyl, ethyl, propyl, isopropyl, butyl, isobutyl, s-butyl, t-butyl, pentyl, hexyl, octyl, and decyl groups, of which $C_1$–$C_{10}$ alkyl groups are typically preferred), alicyclic hydrocarbon groups (e.g., cyclopentyl, cyclohexyl, cyclohexenyl, and other $C_3$–$C_{15}$ cycloalkyl groups or cycloalkenyl groups), and $C_6$–$C_{14}$ aryl groups. Alternatively, preferred are non-aromatic carbon rings each having from about 3 to about 15 members (typically preferably from about 5 to about 8 members) formed by $R^b$ and $R^c$ with the adjacent carbon atom. In addition, non-aromatic carbon rings each having an oxo group bonded thereto and having from about 3 to about 20 members, lactone rings each having from about 4 to about 20 members and lactam rings each having from about 4 to about 20 members formed by Y and $R^b$ or $R^c$ with the adjacent carbon atom are also preferred.

Examples of the compounds represented by Formula (1) each containing an electron attractive group include acetone, methyl ethyl ketone, diethyl ketone, isopropyl methyl ketone, acetophenone, benzyl methyl ketone, acetylacetone, acetoacetic esters (e.g., methyl acetoacetate, ethyl acetoacetate, propyl acetoacetate and isopropyl acetoacetate), α-acetyl-γ-butyrolactone and other chain ketones (including keto-esters and keto-lactones); cyclopentanone, cyclohexanone, cyclooctanone, cyclodecanone, cyclododecanone, cyclotetradecanone, and other cyclic ketones; acetaldehyde, propionaldehyde, phenylacetaldehyde, and other aldehydes; methyl acetate, ethyl acetate, phenyl acetate, methyl propionate, ethyl propionate, methyl butyrate, ethyl butyrate, methyl hexanoate, ethyl hexanoate, methyl phenylacetate, ethyl phenylacetate, malonates (e.g., methyl malonate, ethyl malonate, propyl malonate and isopropyl malonate), adipates, and other esters; β-propiolactone, γ-butyrolactone, δ-valerolactone, ε-caprolactone, and other lactones; phenylacetic acid, adipic acid, and other carboxylic acids; adipic anhydride and other acid anhydrides; N,N-dimethylacetamide, N,N-dimethylpropionamide, and other amides; β-propiolactam, γ-butyrolactam, δ-valerolactam, ε-caprolactam, and other lactams; acetonitrile, propionitrile, malononitrile, ethyl cyanoacetate, and other nitriles; N-isopropylidenebenzylamine, N-isopropylideneaniline, N-(1-methylbutylidene)butylamine, and other imines; nitromethane, nitroethane, and other nitro compounds. Among them, ketones (chain ketones and cyclic ketones), esters, nitrites, lactones, carboxylic acids and acid anhydrides are typically preferred.

[Compounds Having Unsaturated Carbon-carbon Bond]

The compounds each having an unsaturated carbon-carbon bond include olefins represented by Formula (2) and acetylenes represented by Formula (7).

In the olefins represented by Formula (2) and the acetylenes represented by Formula (7), organic groups in $R^d$, $R^e$, $R^f$, $R^g$, $R^i$ and $R^j$ include similar organic groups to those in $R^b$ and $R^c$.

Two of the substituents $R^d$, $R^e$, $R^f$ and $R^g$ may be combined with each other to form a ring with the adjacent one or two carbon atoms. Such rings include, but are not limited to, cyclopropane, cyclobutane, cyclopentane, cyclopentene, cyclohexane, cyclohexene, cyclooctane, cyclododecane, norbornene, and other alicyclic carbon rings (e.g., cycloalkane rings, cycloalkene rings and bridged carbon rings) each having from about 3 to about 20 members. These rings may have substituents and may be condensed with other rings (non-aromatic rings or aromatic rings).

The substituents $R^i$ and $R^j$ may be combined with each other to form a ring with the adjacent two carbon atoms. The ring may have a substituent and may be condensed with another ring (a non-aromatic ring or an aromatic ring).

Preferred $R^d$, $R^e$, $R^f$, $R^g$, $R^i$ and $R^j$ include, for example, hydrogen atom, hydrocarbon groups [e.g., $C_1$–$C_{20}$ aliphatic hydrocarbon groups (typically preferably $C_1$–$C_{10}$ aliphatic hydrocarbon groups), $C_6$–$C_{20}$ aryl groups (e.g., phenyl group and naphthyl group), cycloalkyl groups (e.g., cycloalkyl groups each having from about 3 to about 8 members), haloalkyl groups (e.g., trifluoromethyl group and other $C_1$–$C_6$ haloalkyl groups, of which $C_1$–$C_4$ haloalkyl groups are typically preferred)], heterocyclic groups, substituted oxycarbonyl groups (e.g., $C_1$–$C_6$ alkoxy-carbonyl groups, aryloxycarbonyl groups, aralkyloxycarbonyl groups and cycloalkyloxycarbonyl groups), carboxyl group, substituted or unsubstituted carbamoyl groups, cyano group, nitro group, sulfur acid groups, sulfur acid ester groups, and acyl groups.

The olefins represented by Formula (2) may be any of alpha olefins and internal olefins. The olefins also include dienes and other olefins each having a plurality of carbon-carbon double bonds. Examples of the olefins are ethylene, propylene, 1-butene, 2-butene, isobutene, 1-pentene, 2-pentene, 1-hexene, 2-hexene, 3-hexene, 1-heptene, 1-octene, 2-octene, 3-octene, 4-octene, 1-nonene, 1-decene, 1-dodecene, 1,5-hexadiene, 1,6-heptadiene, 1,7-octadiene, styrene, vinyltoluene, α-methylstyrene, 3-vinylpyridine, 3-vinylfuran, 3-vinylthiophene, and other chain olefins (alkenes); cyclopentene, cyclohexene, cyclooctene, cyclodecene, cyclododecene, norbornene, and other cyclic olefins (cycloalkanes and bridged cyclic hydrocarbons each having a carbon-carbon double bond).

The acetylenes represented by Formula (7) also include diynes and other acetylenes each having a plurality of carbon-carbon triple bonds. Typical examples of the acetylenes are acetylene, 1-propyne, 1-butyne, 2-butyne, 1-pentyne, 1-hexyne, 1-heptyne, 1-octyne and phenylacetylene.

[Catalytic Compounds of Groups 5 to 9 Elements of the Periodic Table of Elements]

According to the present invention, the compounds of Groups 5 to 9 elements of the Periodic Table of Elements are used as catalysts. The Groups 5 to 9 elements of the Periodic Table of Elements include vanadium V, niobium Nb, tantalum Ta, and other Group 5 elements; chromium Cr, molybdenum Mo, tungsten W, and other Group 6 elements; manganese Mn, technetium Tc, rhenium Re, and other Group 7 elements; iron Fe, ruthenium Ru, osmium Os, and other Group 8 elements; cobalt Co, rhodium Rh, iridium Ir, and other Group 9 elements. Among them, manganese Mn and other Group 7 elements are preferred. Preferred elements include metallic elements of the fourth period (vanadium V, chromium Cr, manganese Mn, iron Fe, and cobalt Co). As the catalysts, metallic elements compounds each exhibiting activity in one-electron oxidation are preferred.

The compounds of Groups 5 to 9 elements of the Periodic Table of Elements include, but are not limited to, elementary substances, hydroxides, oxides (including complex oxides), halides (fluorides, chlorides, bromides, and iodides), salts of oxoacids (e.g., nitrates, sulfates, phosphates, borates, and carbonates), oxoacids, isopolyacids, heteropolyacids, and other inorganic compounds of the aforementioned metallic elements; salts of organic acids (e.g., acetates, propionates, prussiates, naphthenates, and stearates), complexes, and other organic compounds of the metallic elements. Ligands for constituting the complexes include OH (hydroxo), alkoxy (e.g., methoxy, ethoxy, propoxy, and butoxy), acyl (e.g., acetyl and propionyl), alkoxycarbonyl (e.g., methoxycarbonyl and ethoxycarbonyl), acetylacetonato, cyclopentadienyl group, halogenatoms (e.g., chlorine and bromine atoms), CO, CN, oxygen atom, $H_2O$ (aquo), phosphines (triphenylphosphine and other triarylphosphines) and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds.

Examples of the compounds-of Groups 5 to 9 elements of the Periodic Table of Elements include, by taking manganese compounds as an example, manganese hydroxide, manganese oxide, manganese chloride, manganese bromide and other manganese halides, manganese nitrate, manganese sulfate, manganese phosphate, manganese carbonate, manganates, permanganates, manganese molybdate, and other heteropolyacids containing manganese or salts thereof, and other inorganic compounds; manganese formate, manganese acetate, manganese propionate, manganese naphthenate, manganese stearate, manganese thiocyanate, and other salts of organic acids, and acetylacetonatomanganese and other complexes, and other organic compounds. Manganese may be divalent or trivalent. Among these manganese compounds, manganese acetate, and other organic acid salts, and acetylacetonatomanganese and other complexes, and other organic manganese compounds are preferred.

Examples of cobalt compounds include, but are not limited to, cobalt hydroxide, cobalt oxide, cobalt chloride, cobalt bromide and other cobalt halides, cobalt nitrate, cobalt sulfate, cobalt phosphate, cobalt molybdate and other heteropolyacids containing cobalt or salts thereof, and other inorganic compounds; cobalt formate, cobalt acetate, cobalt naphthenate, cobalt stearate, and other organic acid salts, and acetylacetonatocobalt and other complexes, and other organic compounds. Cobalt may be divalent or trivalent. Among these cobalt compounds, cobalt acetate and other organic acid salts, and acetylacetonatocobalt and other complexes, and other organic cobalt compounds are typically preferred.

Examples of vanadium compounds are vanadium hydroxide, vanadium oxide, vanadium chloride, vanadyl chloride, vanadium sulfate, vanadyl sulfate, sodium vanadate, and other inorganic compounds; acetylactonatovanadium, vanadyl acetylacetonato, and other complexes, and other vanadium compounds each having a valency of from 2 to 5.

Examples of molybdenum compounds are molybdenum hydroxide, molybdenum oxide, molybdenum chloride, molybdenum bromide, molybdenum sulfide, molybdic acid or salts thereof, phosphomolybdic acid or salts thereof, silicomolybdic acid or salts thereof, and other inorganic compounds; carbonylmolybdenum, bis(acetylacetonato) dioxomolybdenum, chlorotricarbonyl(η-cyclopentadienyl) molybdenum, dibromobis (η-cyclopentadienylmolybdenum, and other complexes, and other molybdenum compounds each having a valency of from 0 to 6. Examples of compounds of the other metallic elements include compounds corresponding to the above-mentioned manganese, vanadium or molybdenum compounds. The valences of the Groups 5 to 9 elements of the Periodic Table of Elements are not specifically limited and are often from about 0 to about 6.

Each of these compounds of Groups 5 to 9 elements of the Periodic Table of Elements can be used alone or in combination. The combination use of two or more types of compounds respectively containing different elements may improve the rate and selectivity of a reaction in some cases. Such combinations include a combination of a manganese compound with another compound of Group 5, 6, 7, 8 or 9 of the Periodic Table of Elements (especially a cobalt compound).

The amount of the catalytic compound (catalyst) of Group 5, 6, 7, 8 or 9 element of the Periodic Table of Elements is, for example, from about 0.0001 to about 0.1 mole, preferably from about 0.0002 to about 0.05 mole, and more preferably from about 0.0005 to about 0.01 mole, relative to 1 mole of the compound used in a less amount between the compound containing an electron attractive group represented by Formula (1) and the compound having an unsaturated carbon-carbon bond [the olefin represented by Formula (2) or the acetylene represented by Formula (7)].

When a manganese compound and a cobalt compound are used in combination, the amount of the manganese compound is, for example, from about 0.0001 to about 0.1 mole, preferably from about 0.0002 to about 0.05 mol, and more preferably from about 0.0005 to about 0.01 mole, relative to 1 mole of the compound used in a less amount between the compound containing an electron attractive group represented by Formula (1) and the compound having an unsaturated carbon-carbon bond [the olefin represented by Formula (2) or the acetylene represented by Formula (7)]. The amount of the cobalt compound is, for example, from about 0.00005 to about 0.1 mole, preferably from about 0.0001 to about 0.01 mole, and more preferably from about 0.002 to about 0.005 mole, relative to 1 mole of the compound used in a less amount between the compound containing an electron attractive group represented by Formula (1) and the compound having an unsaturated carbon-carbon bond [the olefin represented by Formula (2) or the acetylene represented by Formula (7)]. In this case, the molar ratio of the manganese compound to the cobalt compound is generally from about 1/99 to about 99/1, preferably from about 5/95 to about 98/2, more preferably from about 20/80 to 95/5, and especially preferably from about 40/60 to about 95/5.

In order to improve the rate or selectivity of the reaction according to the present invention, the compounds of Groups 5 to 9 elements of the Periodic Table of Elements can be used in combination with the compounds of the other metallic elements, such as transition metals including cerium, titanium, zirconium, nickel, palladium, platinum, copper and zinc.

The reaction system may further comprise azobisisobutyronitrile (AIBN) and other polymerization initiators, radical generators, or radical reaction accelerators [e.g., halogens (e.g., chlorine and bromine), peracids and peroxides]. The presence of such components in the reaction system may accelerate or enhance the reaction in some cases. Alternatively, light irradiation or ultrasound application may increase the reaction rate.

[Oxygen]

As oxygen, nascent oxygen can be used, but molecular oxygen is generally used. Such molecular oxygen may be pure oxygen or oxygen (e.g., air) diluted with an inert gas such as nitrogen, helium, argon or carbon dioxide from the viewpoints of higher operating property and safety. In some cases depending on the type of the substrate and other conditions, the use of a gaseous mixture including oxygen and an inert gas (e.g., nitrogen gas) produces a target compound in a higher yield than the use of pure oxygen. The molar ratio of oxygen to the inert gas in the gaseous mixture is, for example, from about 10/90 to about 95/5, preferably from about 15/85 to about 90/10, and more preferably from about 25/75 to about 80/20.

The amount of oxygen can appropriately be selected depending on the type of the substrate and is generally equal to or more than about 0.5 mole (e.g., equal to or more than about 1 mole), preferably from about 1 to about 100 moles, and more preferably from about 2 to about 50 moles, relative to 1 mole of the compound used in a less amount between the compound containing an electron attractive group represented by Formula (1) and the compound having an unsaturated carbon-carbon bond [the olefin represented by Formula (2) or the acetylene represented by Formula (7)]. Oxygen is often used in excess moles to the substrate.

[Reaction]

The reaction is performed in the presence of, or in the absence of, a solvent. Such solvents include, but are not limited to, acetic acid, propionic acid, and other organic acids; benzonitrile and other nitriles; formamide, acetamide, dimethylformamide (DMF), dimethylacetamide, and other amides; hexane, octane, and other aliphatic hydrocarbons; chloroform, dichloromethane, dichloroethane, carbon tetrachloride, chlorobenzene, trifluoromethylbenzene, and other halogenated hydrocarbons; nitrobenzene and other nitro compounds; and mixtures of these solvents. As the solvents, acetic acid and other organic acids, benzonitrile and other nitriles, and trifluoromethylbenzene and other halogenated hydrocarbons are often used. The substrate (reaction material) can also be used as the solvent.

The molar ratio of the compound containing an electron attractive group represented by Formula (1) to the compound having an unsaturated carbon-carbon bond [the olefin represented by Formula (2) or the acetylene represented by Formula (7)] can appropriately be selected depending on the types of the two compounds and the combination thereof and is generally from about 0.8 to about 50, preferably from about 1.5 to about 30, and more preferably from about 2 to about 20, from the viewpoint of reactivity.

A reaction temperature can appropriately be selected depending on, for example, the types of the compound containing an electron attractive group and the compound having an unsaturated carbon-carbon bond (the olefin or the acetylene) and is, for example, from about 0° C. to about 150° C., and preferably from about 30° C. to about 100° C. The reaction can be performed at atmospheric pressure or under a pressure (under a load). When the reaction is performed under a pressure (under a load), the pressure is generally from about 1 to about 100 atm (from about 0.101 to about 10.1 MPa), and preferably from about 1.5 to about 80 atm (from about 0.152 to about 8.08 MPa). A reaction time can appropriately be selected within a range of from about 30 minutes to about 48 hours, depending on the reaction temperature and pressure. The reaction can be performed in the presence of, or under the flow of, oxygen in a conventional system such as a batch system, semi-batch system or continuos system.

The above process can produce the compound represented by Formula (3) in a good yield. The reaction is supposed to proceed in the following manner. By action of the catalytic compound of Group 5, 6, 7, 8 or 9 element of the Periodic Table of Elements and oxygen, a radical is formed at the alpha position of the electron attractive group of the compound containing the electron attractive group, and then the radical adds to the carbon atom of an unsaturated bond (a double bond or triple bond) of the olefin or the acetylene to yield a compound having a corresponding alkyl group or alkenyl group at the alpha position of the electron attractive group [a compound of Formula (3) or Formula (8) where Z is a hydrogen atom). A compound of Formula (3) or Formula (8) where Z is a hydroxyl group is supposed to be formed in such a manner that the radical at the alpha position of the electron attractive group adds to the olefin or the acetylene and to yield a secondary radical (adduct radical), and the secondary radical further reacts with oxygen. The compound of Formula (3) or Formula (8) where Z is a hydroxyl group is often formed when the partial oxygen pressure in the system is high or when the secondary radical formed by the addition of the radical to the olefin or acetylene is highly stable (e.g., in the case where $R^g$ is an aromatic group).

After the completion of the reaction, the resulting reaction products can easily be separated and purified by a conventional technique such as filtration, concentration, distillation, extraction, crystallization, recrystallization, column chromatography, and other separation means or combinations of these separation means.

When the carbonyl-group-containing compound represented by Formula (1a) is used as the compound containing an electron attractive group, and the compound represented by Formula (2a), i.e., a compound having an aromatic group bonded to a carbon atom constituting a double bond, is used as the olefin, the furanol derivative represented by Formula (4) is formed in a good yield in addition to, or instead of, the compound represented by Formula (3).

This is probably because the radical formed at the alpha position of the electron attractive group adds to the olefin to yield a secondary carbon radical species, which is stabilized by the aromatic ring, and this radical is then allowed to react with oxygen and thereby yields an alcohol represented by following Formula (9):

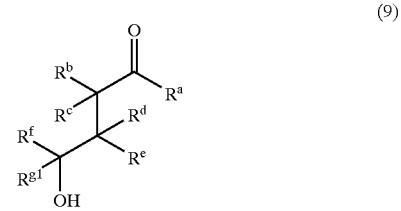

(9)

wherein $R^a$, $R^b$, $R^c$, $R^d$, $R^e$, $R^f$ and $R^{g1}$ have the same meanings as defined above, and the hydroxyl group of the alcohol attacks the carbonyl group and thereby form a ring.

Organic groups in the substituent $R^a$ include similar organic groups to those in $R^b$ and $R^c$. Typical examples of such organic groups are the aforementioned hydrocarbon groups (aliphatic hydrocarbon groups, alicyclic hydrocarbon groups and aromatic hydrocarbon groups) and the aforementioned heterocyclic groups.

In Formulae (1a) and (9), two of $R^a$, $R^b$ and $R^c$ maybe combined with each other to form a ring with adjacent one or two carbon atoms. Rings formed by $R^a$ and $R^b$ or $R^c$ with the adjacent two carbon atoms include, but are not limited to, cyclopentanone ring, cyclohexanone ring, cyclooctanone ring, cyclodecanone ring, cyclododecanone ring, adamantanone ring, and other non-aromatic carbon rings (cycloalkanone rings, cycloalkenone rings and oxo-groupcontaining bridged carbon rings) each having an oxo group bonded thereto and having from about 3 to about 20 members (preferably from about 3 to about 15 members, more preferably from about 5 to about 15 members, and typically preferably from about 5 to about 10 members). Rings formed by $R^b$ and $R^c$ with the adjacent carbon atom include similar rings to those mentioned above.

Typical examples of the compounds represented by Formula (1a) include the aforementioned chain ketones (e.g., methyl ethyl ketone and diethyl ketone), cyclic ketones (e.g., cyclohexanone, cyclooctanone and cyclododecanone), and aldehydes (e.g., propionaldehyde).

Aromatic cyclic rings in the substituent $R^{g1}$ include, but are not limited to, phenyl, naphthyl, and other aromatic hydrocarbon groups each having from about 6 to about 20 carbon atoms; aromatic heterocyclic groups corresponding to aromatic heterocyclic rings such as furan, oxazole, isoxazole, 4-oxo-4H-pyran, benzofuran, isobenzofuran, 4-oxo-4H-chromene, thiophene, thiazole, isothiazole, thiadiazole, 4-oxo-4H-thiopyran, benzothiophene, pyrrole, pyrazole, imidazole, triazole, pyridine, pyridazine, pyrimidine, indole, quinoline, acridine, naphthyridine, quinazoline, and purine. These aromatic cyclic groups may have substituents. Such substituents include similar groups to those which the hydrocarbon groups in $R^b$ and $R^c$ may have.

Typical examples of the compounds represented by Formula (2a) are styrene, vinyltoluene, o-chlorostyrene, m-chlorostyrene, p-chlorostyrene, p-methoxystyrene, α-methylstyrene, 1-propenylbenzene, 1-vinylnaphthalene, 2-vinylnaphthalene, and other compounds each having an aromatic hydrocarbon group carrying a vinyl group (including a substituted vinyl group) bonded thereto; 3-vinylfuran, 3-vinylthiophene, 2-vinylpyridine, 3-vinylpyridine, 4-vinylpyridine, 3-vinylquinoline, and other compounds each having an aromatic heterocyclic group carrying a vinyl group (including a substituted vinyl group) bonded thereto.

The reaction conditions and reaction procedures in the reaction to obtain the furanol derivative represented by Formula (4) are similar to those mentioned above.

[Reaction Between Compound of Formula (5) and Compound of Formula (2) or (7)]

According to the present invention, a ketone having an alkyl group or alkenyl group bonded at the alpha position of the carbonyl group can be produced from a hydrocarbon through one pot by using the above reaction. Specifically, the carbonyl compound represented by Formula (3a) or (8a) can be obtained by allowing the compound having a methylene group represented by Formula (5) to react with the olefin represented by Formula (2) or the acetylene represented by Formula (7) in the presence of the imide compound catalyst represented by Formula (6), the manganese catalyst and oxygen.

In Formula (5), organic groups in $R^b$, $R^c$ and $R^h$ include similar groups to those mentioned above. Preferred $R^b$ and $R^c$ include similar groups to those mentioned above. Preferred $R^h$ includes, but is not limited to, the aromatic cyclic groups (e.g., phenyl, naphthyl, and other aromatic hydrocarbon groups; and aromatic heterocyclic groups corresponding to furan, thiophene, pyridine, and other aromatic heterocyclic rings) mentioned in the substituent $R^{g1}$.

Two of the substituents $R^b$, $R^c$ and $R^h$ may be combined with each other to form a ring with the adjacent one or two carbon atoms. Rings formed by $R^h$ and $R^b$ or $R^c$ with the adjacent two carbon atoms include, but are not limited to, cyclopentane ring, cyclohexane ring, cyclooctane ring, cyclodecane ring, cyclododecane ring, adamantane ring, and other non-aromatic carbon rings (cycloalkane rings, cycloalkene rings, and bridged carbon rings) each having from about 3 to about 20 members (preferably from about 3 to about 15 members, more preferably from about 5 to about 15 members, and typically preferably from about 5 to about 10 members). These rings may have substituents such as the substituents which the hydrocarbon groups may have. Rings formed by $R^b$ and $R^c$ with the adjacent carbon atom include similar rings to those mentioned above.

Typical examples of the compounds represented by Formula (5) are ethylbenzene, propylbenzene, butylbenzene, 3-ethylfuran, 3-ethylthiophene, 2-ethylpyridine, 3-ethylpyridine, 4-ethylpyridine, and other compounds each having a methylene group at the adjacent position to an aromatic ring; cyclopentane, cyclohexane, cyclooctane, cyclodecane, cyclododecane, cyclotetradecane, and other alicyclic compounds.

Of the substituents $R^1$ and $R^2$ in the imide compound catalyst represented by Formula (6), the halogen atom includes iodine, bromine, chlorine and fluorine. The alkyl group includes, but is not limited to, methyl, ethyl, propyl, isopropyl, butyl, isobutyl, s-butyl, t-butyl, pentyl, hexyl, heptyl, octyl, decyl, and other straight- or branched-chain alkyl groups each having from about 1 to about 10 carbon atoms. Preferred alkyl groups are alkyl groups each having from about 1 to about 6 carbon atoms, of which lower alkyl groups each having from about 1 to about 4 carbon atoms are typically preferred.

The aryl group includes phenyl and naphthyl groups, for example. Illustrative cycloalkyl groups include cyclopentyl, and cyclohexyl groups. Illustrative alkoxy groups are methoxy, ethoxy, propoxy, isopropoxy, butoxy, isobutoxy, t-butoxy, pentyloxy, hexyloxy, and other alkoxy groups each having from about 1 to about 10 carbon atoms, and preferably having from about 1 to about 6 carbon atoms. Among them, lower alkoxy groups each having from about 1 to about 4 carbon atoms are typically preferred.

Examples of the alkoxycarbonyl group are methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other alkoxycarbonyl groups each having from about 1 to about 10 carbon atoms in the alkoxy moiety. Preferred alkoxycarbonyl groups are alkoxycarbonyl groups each having from about 1 to about 6 carbon atoms in the alkoxy moiety, of which lower alkoxycarbonyl groups each having from about 1 to about 4 carbon atoms in the alkoxy moiety are typically preferred.

Illustrative acyl groups are formyl, acetyl, propionyl, butyryl, isobutyryl, valeryl, isovaleryl, pivaloyl, and other acyl groups each having from about 1 to about 6 carbon atoms.

The substituents $R^1$ and $R^2$ may be identical to or different from each other. The substituents $R^1$ and $R^2$ in Formula (6) may be combined to form a double bond, or an aromatic or non-aromatic ring. The preferred aromatic or non-aromatic ring has from about 5 to about 12 members, and more preferably from about 6 to about 10 members. The ring may be a heterocyclic ring or condensed heterocyclic ring, but it is often a hydrocarbon ring. Such rings include, for example, non-aromatic alicyclic rings (e.g., cyclohexane ring and other cycloalkane rings which may have a substituent; and cyclohexene ring and other cycloalkene rings which may have a substituent), non-aromatic bridged rings (e.g., 5-norbornene ring and other bridged hydrocarbon rings which may have a substituent), benzene ring, naphthalene ring, and other aromatic rings (including condensed rings) which may have a substituent. The ring comprises an aromatic ring in many cases. The ring may have at least one substituent. Such substituents include, but are not limited to, alkyl groups, haloalkyl groups, hydroxyl group, alkoxy groups, carboxyl group, alkoxycarbonyl groups, acyl groups, nitro group, cyano group, amino group, and halogen atoms.

In Formula (6), X represents an oxygen atom or a hydroxyl group, and the bond between the nitrogen atom N and X is a single bond or a double bond.

One or two of the N-substituted cyclic imido group indicated in Formula (6) may further be formed on $R^1$, $R^2$, or on the double bond or aromatic or non-aromatic ring formed together by $R^1$ and $R^2$. For example, when $R^1$ or $R^2$ is an alkyl group having two or more carbon atoms, the N-substituted cyclic imido group may be formed together with the adjacent two carbon atoms constituting the alkyl group. Likewise, when $R^1$ and $R^2$ are combined to form a double bond, the N-substituted cyclic imido group may be formed together with the double bond. In case that $R^1$ and $R^2$ are combined to form an aromatic or non-aromatic ring, the N-substituted cyclic imido group may be formed with the adjacent two carbon atoms constituting the ring.

Preferred imide compounds include compounds of the following formulae:

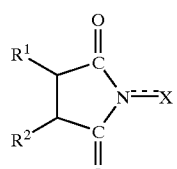

(6a)

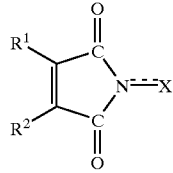

(6b)

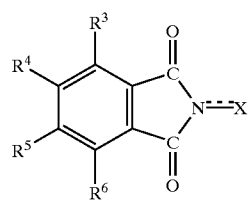

(6c)

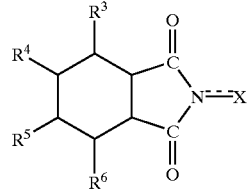

(6d)

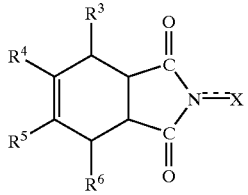

(6e)

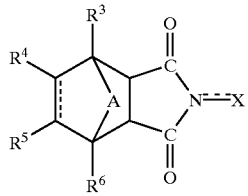

(6f)

wherein $R^3$ to $R^6$ are the same or different and are each a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom, where adjacent groups of $R^3$ to $R^6$ may be combined to form an aromatic or non-aromatic ring; in Formula (6f), A is a methylene group or an oxygen atom; and $R^1$, $R^2$ and X have the same meanings as defined above, where one or two of N-substituted cyclic imido group indicated in Formula (6c) may further be formed on the benzene ring in Formula (6c).

In the substituents $R^3$ to $R^6$, the alkyl group includes similar alkyl groups to those exemplified above, of which alkyl groups each having from about 1 to about 6 carbon atoms are typically preferred. The haloalkyl group includes trifluoromethyl group and other haloalkyl groups each having from about 1 to about 4 carbon atoms. The alkoxy group includes similar alkoxy groups to those mentioned above, of which lower alkoxy groups each having from about 1 to about 4 carbon atoms are typically preferred. The alkoxycarbonyl group includes similar alkoxycarbonyl groups to those described above, of which lower alkoxycarbonyl groups each having from about 1 to about 4 carbon atoms in the alkoxy moiety are typically preferred. The acyl group includes similar acyl groups to those described above, of which acyl groups each having from about 1 to about 6 carbon atoms are typically preferred. The halogen atom includes fluorine, chlorine and bromine atoms. Each of the substituents $R^3$ to $R^6$ is often a hydrogen atom, a lower alkyl group having from about 1 to about 4 carbon atoms, a carboxyl group, a nitro group, or a halogen atom. The ring formed together by $R^3$ to $R^6$ includes similar rings to the aforementioned rings which are formed together by $R^1$ and $R^2$. Among them, aromatic or non-aromatic 5-to 12-membered rings are typically preferred.

Examples of preferred imide compounds include N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphthalenetetracarboximide.

The imide compounds represented by Formula (6) can be prepared by a conventional imidation process (a process for the formation of an imide), such as a process that comprises the steps of allowing a corresponding acid anhydride to react with hydroxylamine $NH_2OH$ for ring-opening of an acid anhydride group, and closing the ring to form an imide.

Such acid anhydrides include, but are not limited to, succinic anhydride, maleic anhydride, and other saturated or unsaturated aliphatic dicarboxylic anhydrides, tetrahydrophthalic anhydride, hexahydrophthalic anhydride (1,2-cyclohexanedicarboxylic anhydride), 1,2,3,4-cyclohexanetetracarboxylic 1,2-dianhydride, and other saturated or unsaturated non-aromatic cyclic polycarboxylic anhydrides (alicyclic polycarboxylic anhydrides), HET anhydride (chlorendic anhydride), himic anhydride, and other bridged cyclic polycarboxylic anhydrides (alicyclic polycarboxylic anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8;4,5-naphthalenetetracarboxylic dianhydride, and other aromatic polycarboxylic anhydrides.

Typically preferred imide compounds include N-hydroxyimide compounds derived from alicyclic polycarboxylic anhydrides or aromatic polycarboxylic anhydrides, of which N-hydroxyphthalimide and other N-hydroxyimide compounds derived from aromatic polycarboxylic anhydrides are typically preferred.

Each of the imide compounds represented by Formula (6) can be used alone or in combination. The imide compounds can be used as being supported on a carrier. As such carriers, activated carbon, zeolite, silica, silica-alumina, bentonite, and other porous carries are often used.

The amount of the imide compound can be selected within a wide range and is, for example, from about 0.0001 to about 1 mole, preferably from about 0.001 to about 0.5 mole, and more preferably from about 0.01 to about 0.4 mole, relative to 1 mole of the compound having a methylene group represented by Formula (5).

As the catalytic compound of Group 5, 6, 7, 8 or 9 element of the Periodic Table of Elements (e.g., a manganese catalyst), similar catalysts to those mentioned above can be used. Likewise, each of the catalytic compounds of Groups 5 to 9 elements of the Periodic Table of Elements can be used alone or in combination and can be used in combination with transition metal compounds or other metallic compounds. Specifically, by using a manganese catalyst in combination with a cobalt catalyst and/or a vanadium catalyst, the reaction very smoothly proceeds.

The amount of the catalytic compound of Group 5, 6, 7, 8 or 9 element of the Periodic Table of Elements is, for example, from about 0.0001 to about 0.1 mole, preferably from about 0.0002 to about 0.05 mole, and more preferably from about 0.0005 to about 0.01 mole, relative to 1 mole of the compound used in a less amount between the compound represented by Formula (5) and the compound represented by Formula (2) or (7).

When a manganese catalyst is used in combination with a cobalt catalyst and/or a vanadium catalyst, the amount of the manganese catalyst is, for example, from about 0.0001 to about 0.1 mole, preferably from about 0.0002 to about 0.05 mole, and more preferably from about 0.0005 to about 0.01 mole, relative to 1 mole of the compound used in a less amount between the compound represented by Formula (5) and the compound represented by Formula (2) or (7). The total amount of the cobalt catalyst and vanadium catalyst is, for example, from about 0.00005 to about 0.1 mole, preferably from about 0.0001 to about 0.01 mole, and more preferably from about 0.0002 to about 0.005 mole, relative to 1 mole the compound used in a less amount between the compound represented by Formula (5) and the compound represented by Formula (2) or (7). When the manganese catalyst is used in combination with the cobalt catalyst and/or vanadium catalyst, the molar ratio of the manganese catalyst to the total of the cobalt catalyst and vanadium catalyst is from about 1/99 to about 99/1, preferably from about 5/95 to about 98/2, more preferably from about 20/80 to about 95/5, and specifically preferably from about 40/60 to 95/5.

As is described above, the reaction system may further comprise azobisisobutyronitrile (AIBN) and other polymerization initiators, radical generators, or radical reaction accelerators [e.g., halogens (e.g., chlorine and bromine), peracids, and peroxides]. Alternatively, light or ultrasound may be applied to the reaction system.

Oxygen may be pure oxygen or a gaseous mixture (e.g., air) with an inert gas, as described in the above procedure. The amount of oxygen can appropriately be selected depending on the type of the substrate and is generally equal to or more than about 0.5 mole (e.g., equal to or more than about 1 mole), preferably from about 1 to about 100 moles, and more preferably from about 2 to about 50 moles, relative to 1 mole of the compound used in a less amount between the compound represented by Formula (5) and the compound having an unsaturated carbon-carbon bond [the olefin represented by Formula (2) or the acetylene represented by Formula (7)]. Oxygen is often used in excess moles to the substrate.

The reaction is performed in the presence of, or in the absence of, a solvent. Such solvent include, but are not limited to, acetic acid, propionic acid, and other organic acids; benzonitrile and other nitrites; formamide, acetamide, dimethylformamide (DMF), dimethylacetamide, and other amides; hexane, octane, and other aliphatic hydrocarbons; chloroform, dichloromethane, dichloroethane, carbon tetrachloride, chlorobenzene, trifluoromethylbenzene, and other halogenated hydrocarbons; nitrobenzene and other nitro compounds; and mixtures of these solvents. As the solvents, acetic acid and other organic acids, benzonitrile and other nitriles, and trifluoromethylbenzene and other halogenated hydrocarbons are often used. The substrate (reaction material) can also be used as the solvent.

The molar ratio of the compound having a methylene group represented by Formula (5) to the compound having an unsaturated carbon-carbon bond [the olefin represented by Formula (2) or the acetylene represented by Formula (7)] can appropriately be selected depending on the types of the two compounds and the combination thereof and is generally from about 0.8 to about 50, preferably from about 1.5 to about 30, and more preferably from about 5 to about 15, from the viewpoint of reactivity.

A reaction temperature can appropriately be selected depending on the types of the compound having a methylene group and the olefin or the acetylene and is, for example, from about 0° C. to about 150° C., and preferably from about 30° C. to about 100° C. The reaction can be performed at atmospheric pressure or under a pressure (under a load). When the reaction is performed under a pressure (under a load), the pressure is generally from about 1 to about 100 atm (from about 0.101 to about 10.1 MPa), and preferably from bout 1.5 to about 80 atm (from about 0.152 to about 8.08 MPa). A reaction time can appropriately be selected within a range of from about 30 minutes to about 48 hours depending on the reaction temperature and pressure. The reaction can be performed in the presence of, or under the flow of, oxygen in a conventional system such as a batch system, semi-batch system or continues system.

Reaction operations are not specifically limited, but preferred are the following processes: (i) a process in which a mixture containing the compound having a methylene group represented by Formula (5), the compound having an unsaturated carbon-carbon bond [the olefin represented by Formula (2) or the acetylene represented by Formula (7)], the imide compound catalyst and the catalytic compound of Group 5, 6, 7, 8 or 9 element of the Periodic Table of Elements (e.g., a manganese catalyst and a cobalt catalyst and/or vanadium catalyst) is stirred in an atmosphere of an oxygen-containing gas; and (ii) a process in which a mixture containing the compound having a methylene group represented by Formula (5), the imide catalytic compound and, preferably, the catalytic compound of Group 5, 6, 7, 8 or 9 element of the Periodic Table of Elements (e.g., a cobalt catalyst and/or vanadium catalyst, or the manganese catalyst and the cobalt catalyst and/or vanadium catalyst) is stirred in an atmosphere of an oxygen-containing gas for a predetermined time (e.g., from about 30 minutes to about 24 hours), and to the resulting mixture, the compound having an unsaturated carbon-carbon bond [the olefin represented by Formula (2) or the acetylene represented by Formula (7)] and the catalytic compound of Group 5, 6, 7, 8 or 9 element of the Periodic Table of Elements (e.g., the manganese catalyst, or the manganese catalyst and the cobalt catalyst and/or vanadium catalyst) is added and is further stirred for a predetermined time (e.g., from about 30 minutes to about 24 hours). In the process (ii), when the catalytic compound of Group 5, 6, 7, 8 or 9 element of the Periodic Table of Elements is added in the former step, it is not always required in the latter step. In the process (ii), the atmosphere, pressure, temperature and other conditions of the reaction can appropriately changed in the latter step from those in the former step.

In the above process, the reaction is supposed to proceed in the following manner. The compound having a methylene group represented by Formula (5) is oxidized with oxygen by the action of the imide compound catalyst to yield a carbonyl compound in which the methylene group is converted into a carbonyl group. By action of the manganese catalyst and oxygen, a radical is formed at the alpha position of the carbonyl compound as described above, the radical adds to the carbon atom of a double bond of the olefin or a triple bond of the acetylene to yield the target carbonyl compound represented by Formula (3a) or (8a).

After the completion of the reaction, the resulting reaction products can easily be separated and purified by a conventional technique such as filtration, concentration, distillation, extraction, crystallization, recrystallization, column chromatography, and other separation means or combinations of these separation means.

INDUSTRIAL APPLICABILITY

The process of the present invention can efficiently produce a compound having an alkyl group or alkenyl group bonded at the alpha position of an electron attractive group, or a derivative thereof, by catalytic radical addition reaction. The process can produce a compound having an alkyl group or alkenyl group bonded at the alpha position of an electron attractive group, or a derivative thereof, with a high selectivity from a compound having the electron attractive group, such as a ketone, and an olefin or acetylene. In addition, the process can produce a carbonyl compound having an alkyl group or alkenyl group bonded at the alpha position of a carbonyl group through one pot from a hydrocarbon having a methylene group.

EXAMPLES

The present invention will be illustrated in further detail with reference to several examples below, which are not intended to limit the scope of the invention. In the following examples, reaction products were analyzed by gas chromatography or high performance liquid chromatography. Yields were calculated on the basis of the compound having an unsaturated carbon-carbon bond (the olefin or acetylene).

Example 1

A mixture of 20 mmol of cyclohexanone, 2 mmol of 1-octene, 0.01 mmol of manganese(II) acetate and 2 ml of acetic acid was stirred at 80° C. in an atmosphere of air (1 atm=0.101 MPa) for 5 hours. The resulting reaction mixture was analyzed to find that α-octylcyclohexanone was produced in a yield of 23% with a conversion from 1-octene of 37%.

Example 2

A mixture of 20 mmol of cyclohexanone, 2 mmol of 1-octene, 0.01 mmol of acetylacetonatomanganese(III) [Mn (acac)$_3$] and 2 ml of acetic acid was stirred at 80° C. in an atmosphere of air (1 atm=0.101 MPa) for 5 hours. The resulting reaction mixture was analyzed to find that α-octylcyclohexanone was produced in a yield of 12% with a conversion from 1-octene of 17%.

A reaction was performed in a similar manner as above in an atmosphere of nitrogen gas for 12 hours, and α-octylcyclohexanone was produced in little amount with a conversion from 1-octene of 22%.

Example 3

A mixture of 20 mmol of cyclohexanone, 2 mmol of 1-octene, 0.01 mmol of manganese(II) acetate, 0.002 mmol of cobalt (II) acetate and 0.5 ml of acetic acid was stirred at 80° C. in an atmosphere of air (1 atm=0.101 MPa) for 10 hours. The resulting reaction mixture was analyzed to find that α-octylcyclohexanone was produced in a yield of 45% with conversions from 1-octene and from cyclohexanone of 57% and 9.9%, respectively.

Example 4

A mixture of 20 mmol of cyclohexanone, 2 mmol of 1-octene, 0.01 mmol of manganese(II) acetate, 0.002 mmol of cobalt (II) acetate and 2 ml of acetic acid was stirred at 80° C. in an atmosphere of a gaseous mixture of oxygen and nitrogen (molar ratio 1:1) (1 atm=0.101 MPa) for 10 hours. The resulting reaction mixture was analyzed to find that α-octylcyclohexanone was produced in a yield of 64% with conversions from 1-octene and from cyclohexanone of 72% and 15.8%, respectively.

Example 5

A mixture of 20 mmol of cyclohexanone, 2 mmol of 1-octene, 0.01 mmol of manganese(II) acetate, 0.002 mmol of cobalt (II) acetate and 2 ml of acetic acid was stirred at 0° C. in an atmosphere of a gaseous mixture of oxygen and nitrogen (molar ratio 2:1) (1 atm=0.101 MPa) for 10 hours. The resulting reaction mixture was analyzed to find that α-octylcyclohexanone was produced in a yield of 58% with a conversion from 1-octene and from cyclohexanone of 69% and 19.6%, respectively.

Example 6

A mixture of 20 mmol of cyclohexanone, 2 mmol of 2-octene, 0.01 mmol of manganese (II) acetate, 0.002 mmol of cobalt (II) acetate and 0.5 ml of acetic acid was stirred at 80° C. in an atmosphere of air (1 atm=0.101 MPa) for 10 hours. The resulting reaction mixture was analyzed to find that α-(1-methylheptyl)cyclohexanone and α-(1-ethylhexyl) cyclohexanone were produced in yields of 21% and 16%, respectively, with a conversion from 2-octene of 46%.

Example 7

A mixture of 20 mmol of cyclopentanone, 2 mmol of 1-octene, 0.01 mmol of manganese(II) acetate, 0.002 mmol of cobalt (II) acetate and 1 ml of acetic acid was stirred at 80° C. in an atmosphere of a gaseous mixture of oxygen and nitrogen (molar ratio 1:1) (1 atm=0.101 MPa) for 10 hours. The resulting reaction mixture was analyzed to find that α-octylcyclopentanone was produced in a yield of 66% with a conversion from 1-octene of 78%.

Example 8

A mixture of 10 mmol of cyclooctanone, 2 mmol of 1-octene, 0.01 mmol of manganese(II) acetate, 0.002 mmol of cobalt (II) acetate and 1 ml of acetic acid was stirred at 80° C. in an atmosphere of a gaseous mixture of oxygen and nitrogen (molar ratio 1:1) (1 atm=0.101 MPa) for 10 hours. The resulting reaction mixture was analyzed to find that α-octylcyclooctanone was produced in a yield of 51% with a conversion from 1-octene of 64%.

Example 9

A mixture of 20 mmol of diethyl ketone, 2 mmol of 1-octene, 0.01 mmol of manganese(II) acetate, 0.002 mmol of cobalt (II) acetate and 1 ml of acetic acid was stirred at 80° C. in an atmosphere of air (1 atm=0.101 MPa) for 10 hours. The resulting reaction mixture was analyzed to find that 4-methyl-3-dodecanone was produced in a yield of 56% with a conversion from 1-octene of 62%.

Example 10

A mixture of 20 mmol of acetophenone, 2 mmol of 1-octene, 0.01 mmol of manganese (II) acetate, 0.002 mmol of cobalt (II) acetate and 1 ml of acetic acid was stirred at 100° C. in an atmosphere of oxygen gas (1 atm=0.101 MPa) for 10 hours. The resulting reaction mixture was analyzed to find that 3-hydroxynonyl phenyl ketone was produced in a yield of 44% with a conversion from 1-octene of 50%.

Example 11

A mixture of 15 mmol of cyclohexanone, 3 mmol of styrene, 0.03 mmol of manganese (II) acetate, 0.003 mmol of cobalt (II) acetate and 1.5 ml of acetic acid was stirred at 80° C. in an atmosphere of air (1 atm=0.101 MPa) for 5 hours. The resulting reaction mixture was analyzed to find that a furanol derivative represented by the following formula (1-hydroxy-3-phenyl-2-oxabicyclo[4.3.0]nonane) was produced in a yield of 70% with a conversion from styrene of equal to or more than 98%.

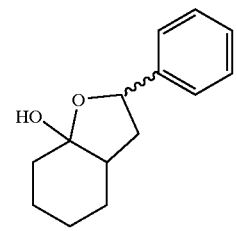

Example 12

A mixture of 20 mmol of cyclooctane, 0.4 mmol of N-hydroxyphthalimide, 0.01 mmol of cobalt(II) acetate and 4 ml of acetic acid was stirred at 80° C. in an atmosphere of oxygen gas (1 atm=0.101 MPa) for 3 hours. To the resulting mixture, 2 mmol of 1-octene and 0.002 mmol of manganese (II) acetate were added and were stirred at 80° C. in an atmosphere of air (1 atm=0.101 MPa) over night. The resulting reaction mixture was analyzed to find that α-octylcyclooctanone was produced in a yield of 10%.

Example 13

A mixture of 20 mmol of cyclohexane, 2-mmol of 1-octene, 2 mmol of N-hydroxyphthalimide, 0.01 mmol of manganese(II) acetate, 0.002 mmol of cobalt(II) acetate and 1 ml of acetic acid was stirred at 80° C. in an atmosphere of oxygen gas (1 atm=0.101 MPa) for 10 hours. The resulting reaction mixture was analyzed to find that 2-octylcyclohexanone was produced in a yield of 15% with a conversion from 1-octene of 85%.

Example 14

A mixture of 20 mmol of cyclohexanone, 2 mmol of 1-octyne, 0.01 mmol of manganese(II) acetate, 0.002 mmol of cobalt (II) acetate and 2 ml of acetic acid was stirred at 50° C. in an atmosphere of air (1 atm=0.101 MPa) for 8 hours. The resulting reaction mixture was analyzed to find that trans-2-(1-octenyl)cyclohexanone and cis-2-(1-octenyl) cyclohexanone were produced in yields of 16% and 13%, respectively, with a conversion from 1-octyne of 45%.

Example 15

A mixture of 20 mmol of cyclohexanone, 2 mmol of phenylacetylene, 0.01 mmol of manganese(II) acetate, 0.002 mmol of cobalt(II) acetate and 2 ml of acetic acid was stirred at 50° C. in an atmosphere of air (1 atm=0.101 MPa) for 8 hours. The resulting reaction mixture was analyzed to find that 2-(2-phenyl-1-ethenyl)cyclohexanone was produced in a yield of 20% with a conversion from phenylacetylene of 99%.

Example 16

A mixture of 30 mmol of α-acetyl-γ-butyrolactone, 2 mmol of 1-octene, 0.1 mmol of manganese(II) acetate, 0.04 mmol of cobalt(II) acetate and 2 ml of acetic acid was stirred at 90° C. in an atmosphere of a gaseous mixture of nitrogen and oxygen (9:1) (1 atm=0.101 MPa) for 14 hours. The resulting reaction mixture was analyzed to find that α-acetyl-α-octyl-γ-butyrolactone was produced in a yield of 71% with a conversion from 1-octene of 91%.

Example 17

A mixture of 30 mmol of ethyl acetoacetate, 2 mmol of 1-octene, 0.1 mmol of manganese(II) acetate, 0.04 mmol of cobalt(II) acetate and 2 ml of acetic acid was stirred at 90° C. in an atmosphere of a gaseous mixture of nitrogen and oxygen (9:1) (1 atm 0.101 MPa) for 5 hours. The resulting reaction mixture was analyzed to find that ethyl 2-octylacetoacetate was produced in a yield of 49% with a conversion from 1-octene of 83%.

Example 18

A mixture of 30 mmol of dimethyl malonate, 2 mmol of 1-octene, 0.04 mmol of manganese(II) acetate, 0.01 mmol of cobalt(II) acetate and 2 ml of acetic acid was stirred at 90° C. in an atmosphere of a gaseous mixture of nitrogen and oxygen (9:1) (1 atm=0.101 MPa) for 3 hours. The resulting reaction mixture was analyzed to find that dimethyl 2-octylmalonate (yield: 56%), dimethyl 2-(2-oxooctyl) malonate (trace amount), α-methoxycarbonyl-γ-hexyl-γ-butyrolactone (yield: 6%), dimethyl 2-(2-octyloctyl) malonate (yield: 5%) and dimethyl 2,2-dioctylmalonate (yield: 3%) were produced with a conversion from 1-octene of 96%.

Example 19

A mixture of 30 mmol of dimethyl malonate, 2 mmol of 1-octene, 0.04 mmol of manganese(II) acetate, 0.002 mmol of zirconium hydroxyacetate and 2 ml of acetic acid was stirred at 90° C. in an atmosphere of a gaseous mixture of nitrogen and oxygen (9:1) (1 atm=0.101 MPa) for 3 hours. The resulting reaction mixture was analyzed to find that dimethyl 2-octylmalonate (yield: 22%), dimethyl 2-(2-oxooctyl)malonate (trace amount), α-methoxycarbonyl-γ-hexyl-γ-butyrolactone (trace amount), dimethyl 2-(2-octyloctyl)malonate (yield: 6%) and dimethyl 2,2-dioctylmalonate (yield: 2%) were produced with a conversion from 1-octene of 60%.

Example 20

A mixture of 20 mmol of dimethyl 2-methoxymalonate, 2 mmol of 1-octene, 0.1 mmol of manganese(II) acetate, 0.002 mmol of cobalt(II) acetate and 2 ml of acetic acid was stirred at 90° C. in an atmosphere of air (1 atm=0.101 MPa) for 3 hours. The resulting reaction mixture was analyzed to find that dimethyl 2-octyl-2-methoxymalonate was produced in a yield of 12% with a conversion from 1-octene of 23%.

Example 21

A mixture of 20 mmol of dimethyl 2-methylmalonate, 2 mmol of 1-octene, 0.04 mmol of manganese(II) acetate, 0.002 mmol of cobalt(II) acetate and 2 ml of acetic acid was stirred at 90° C. in an atmosphere of a gaseous mixture of nitrogen and oxygen (9:1) (1 atm=0.101 MPa) for 3 hours. The resulting reaction mixture was analyzed to find that dimethyl 2-octyl-2-methylmalonate was produced in a yield of 16% with a conversion from 1-octene of 43%.

Example 22

A mixture of 30 mmol of malononitrile, 2 mmol of 1-octene, 0.04 mmol of manganese(II) acetate, 0.002 mmol of cobalt(II) acetate and 2 ml of acetic acid was stirred at 90° C. in an atmosphere of a gaseous mixture of nitrogen and oxygen (9:1) (1 atm=0.101 MPa) for 5 hours. The resulting reaction mixture was analyzed to find that 2-octylmalononitrile was produced in a yield of 14% with a conversion from 1-octene of 79%.

Example 23

A mixture of 30 mmol of dimethyl malonate, 2 mmol of norbornene, 0.04 mmol of manganese (II) acetate, 0.002 mmol of cobalt(II) acetate and 2 ml of acetic acid was stirred at 90° C. in an atmosphere of air (1 atm=0.101 MPa) for 5 hours. The resulting reaction mixture was analyzed to find that dimethyl 2-(2-norbornyl)malonate was produced in a yield of 62% with a conversion from norbornene of 99%.

Example 24

A mixture of 20 mmol of ε-caprolactone, 2 mmol of 1-octene, 0.04 mmol of manganese(II) acetate, 0.002 mmol of cobalt (II) acetate and 2 ml of acetic acid was stirred at 90° C. in an atmosphere of a gaseous mixture of nitrogen and oxygen (9:1) (1 atm=0.101 MPa) for 3 hours. The resulting reaction mixture was analyzed to find that α-octyl-ε-caprolactone was produced in a yield of 32% with a conversion from 1-octene of 68%.

Example 25

A mixture of 20 mmol of adipic anhydride, 2 mmol of 1-octene, 0.04 mmol of manganese (II) acetate, 0.002 mmol of cobalt (II) 0 acetate and 2 ml of acetic acid was stirred at 90° C. in an atmosphere of a gaseous mixture of nitrogen and oxygen (9:1) (1 atm=0.101 MPa) for 3 hours. The resulting reaction mixture was analyzed to find that 2-octyladipic anhydride and 2,5-dioctyladipic anhydride were produced in yields of 29% and 2%, respectively, with a conversion from 1-octene of 63%.

Example 26

A mixture of 20 mmol of dimethyl adipate, 2 mmol of 1-octene, 0.04 mmol of manganese(II) acetate, 0.002 mmol of cobalt (II) acetate and 2 ml of acetic acid was stirred at 90° C. in an atmosphere of a gaseous mixture of nitrogen and oxygen (9:1) (1 atm=0.101 MPa) for 3 hours. The resulting reaction mixture was analyzed to find that dimethyl 2-octyladipate and dimethyl 2,5-dioctyladipate were produced in yields of 36% and 2%, respectively, with a conversion from 1-octene of 60%.

Example 27

A mixture of 20 mmol of adipic acid, 2 mmol of 1-octene, 0.04 mmol of manganese(II) acetate, 0.002 mmol of cobalt (II) acetate and 2 ml of acetic acid was stirred at 90° C. in an atmosphere of a gaseous mixture of nitrogen and oxygen (9:1) (1 atm=0.101 MPa) for 3 hours. The resulting reaction mixture was analyzed to find that 2-octyladipic acid and 2, 5-dioctyladipic acid were produced in yields of 14% and 1%, respectively, with a conversion from 1-octene of 33%.

What is claimed is:

1. In a process for producing an organic compound having an alkyl or alkenyl group in the α-position of an electron attractive group, said organic compound being represented by following Formula (3) or (8):

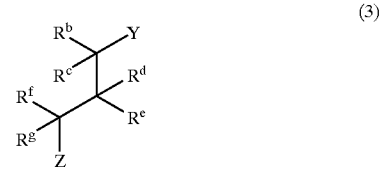

(8)

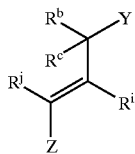

wherein $R^b$ is a hydrogen atom or an organic group, $R^c$ is a hydrogen atom or an organic group, Y is an electron attractive group, $R^b$, $R^c$, and Y may be combined with each other to form a ring with an adjacent carbon atom, each of $R^d$, $R^e$, $R^f$, and $R^g$ is independently a hydrogen atom or an organic group and $R^d$, $R^e$, $R^f$, and $R^g$ may be combined with each other to form a ring with one or two adjacent carbon atoms, $R^i$ is a hydrogen atom or an organic group, $R^j$ is a hydrogen atom or an organic group, and $R^i$ and $R^j$ may be combined with each other to form a ring with two adjacent carbon atoms, and Z is a hydrogen atom or a hydroxyl group, said process comprising the step of reacting a compound containing an electron attractive group represented by following Formula (1):

(1)

wherein $R^b$, $R^c$, and Y are as defined above with a compound containing an unsaturated carbon-carbon bond represented by following Formula (2) or (7):

(2)

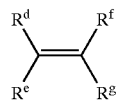

(7)

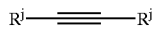

wherein $R^d$, $R^e$, $R^f$, $R^g$, $R^i$ and $R^j$ are as defined above, wherein the improvement comprises conducting said process in the presence of oxygen and a catalytic compound of a Group 7, 8, or 9 element of the Periodic Table of Elements.

2. The process of claim 1, wherein the compound of Formula (1) is selected from the group consisting of ketones, esters, nitriles, lactones, carboxylic acids, and carboxylic acid anhydrides.

3. The process of claim 2, wherein the compound of Formula (1) is selected from the group consisting of cyclohexanone, cyclopentanone, cyclooctanone, diethylketone, acetophenone, α-acetyl-γ-butyrolactone, ethyl acetoacetate, dimethyl malonate, dimethyl 2-methoxymalonate, dimethyl 2-methylmalonate, malonitrile, ε-caprolactone, adipic anydride, dimethyl adipate, and adipic acid.

4. The process of claim 1, wherein the compound of Formula (2) is selected from the group consisting of alkenes and of cycloalkanes and bridged cyclic hydrocarbons each having a carbon-carbon double bond, and wherein the compound of Formula (7) is selected from the group consisting of acetylenes.

5. The process of claim 4, wherein the compound of Formula (2) is selected from the group consisting of 1-octene, 2-octene, and norbornene, and wherein the compound of Formula (7) is selected from the group consisting of 1-octyne and phenylacetylene.

6. The process of claim 1, wherein said catalytic compound of a Group 7, 8 or 9 element of the Periodic Table of Elements comprises a manganese compound used in combination with another compound selected from Group 7, 8, and 9 elements of the Periodic Table of Elements.

7. The process of claim 6, wherein the compound other than manganese is a cobalt compound.

8. The process of claim 1, wherein said oxygen is molecular oxygen diluted with an inert gas.

* * * * *